United States Patent [19]

Pelosi, Jr. et al.

[11] 4,028,374
[45] June 7, 1977

[54] ANTIBACTERIAL THIOCYANATOBENZOTHIAZOLES

[75] Inventors: Stanford Salvatore Pelosi, Jr.; Robert James Alaimo, both of Norwich, N.Y.

[73] Assignee: Morton-Norwich Products, Inc., Norwich, N.Y.

[22] Filed: Nov. 3, 1975

[21] Appl. No.: 628,314

[52] U.S. Cl. .................. 260/305; 424/270
[51] Int. Cl.² ........................ C07D 277/82
[58] Field of Search .................. 260/305

[56] References Cited
UNITED STATES PATENTS

| | | | |
|---|---|---|---|
| 3,551,441 | 12/1970 | Zakaria | 260/305 |
| 3,932,434 | 1/1976 | Paget | 260/305 |
| 3,932,435 | 1/1976 | Lavagnino | 260/305 |

Primary Examiner—Donald G. Daus
Assistant Examiner—Mark L. Berch
Attorney, Agent, or Firm—Anthony J. Franze

[57] ABSTRACT

Certain thiocyanatobenzothiazoles of the formula:

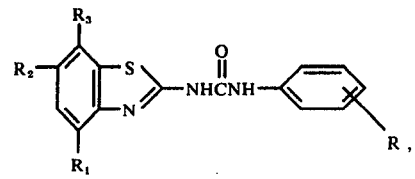

wherein R is hydrogen, 4-bromo, 4-chloro, 4-fluoro, 3,4-dichloro or 4-nitro; $R_1$ is methoxy or thiocyanato; $R_2$ is n-butyl, chloro, methyl, or thiocyanato; and $R_3$ is hydrogen or chloro are effective antibacterial agents.

10 Claims, No Drawings

ANTIBACTERIAL THIOCYANATOBENZOTHIAZOLES

This invention relates to chemical compounds. More particularly this invention relates to certain thiocyanatobenzothiazoles of the formula:

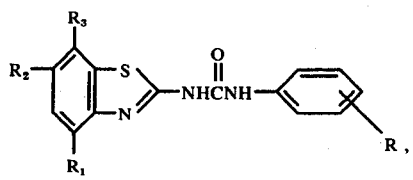

wherein R is hydrogen; 4-bromo, 4-chloro, 4-fluoro, 3,4-dichloro, or 4-nitro; $R_1$ is methoxy or thiocyanato; $R_2$ is n-butyl, chloro, methyl, or thiocyanato; and $R_3$ is hydrogen or chloro and a method for their preparation.

The compounds of this invention possess antibacterial activity. They are particularly inimical to *Staphylococcus aureus and Corynebacterium liquefacieus* in the commonly employed in vitro technique for determining antibacterial activity at levels of from 0.048 to 12.5 meg of compound per milliliter of test media. They are thus adapted to be combined in various forms such as ointments, powders, solutions, sprays, dusts and the like in a concentration of from 0.1–1% by weight suitable for application to prevent bacterial contamination.

The compounds of this invention are readily prepared. Currently it is preferred to react the appropriate aniline with an alkali thiocyanate, such as sodium, in the presence of bromine in an alkanol carrier saturated with sodium bromide. Formation of the urea is then accomplished in conventional fashion by reaction of the 2-aminobenzothiazole with a phenyl isocyanate.

In order that this invention may be fully available to and understood by those skilled in the art, the following examples are supplied.

EXAMPLE I

6-Methyl-2[3-(p-nitrophenyl)ureido]-4-thiocyanatobenzothiazole

A mixture of 2-amino-6-methyl-4-thiocyanatobenzothiazole (35 g., 0.16 mole) in dimethylformamide (250ml.) was treated slowly with p-nitrophenyl isocyanate (27 g., 0.16 mole). The reaction was then heated under stirring on the steam bath for 5 hours. The mixture was then filtered hot. The solution was chilled in an ice bath and filtered. The product was combined with the solid initially filtered to give 40 g. (65%) of off-white solid.

Recrystallization from ethanol-dimethylformamide provided an analytical sample which melted at 283°–284°.

Anal. Calcd. for $C_{16}H_{11}N_5O_3S_2$: C, 49.86; H, 2.88; N, 18.17.

Found: C, 49.73; H, 2.90; N, 18.12.

EXAMPLE II

6-Chloro-2-(3-phenylureido)-4-thiocyanatobenzothiazole

A mixture of sodium thiocyanate (200 g., 2.5 moles) in anhydrous methanol (1200 ml.) was chilled to −7° in a dry ice-acetone bath. To the stirred mixture was added dropwise a chilled solution of bromine (200 g., 1.25 moles) in sodium bromide saturated methanol (300 ml.). The temperature is maintained between −7° and −10° throughout the addition. After the addition was complete, p-chloroaniline (65 g., 0.5 mole) was poured into the mixture and the stirring continued at room temperature overnight.

The reaction mixture was filtered and the solution poured into water (3.1) and made basic with $NH_4OH$ to precipitate 2-amino-6-chloro-4-thiocyanatobenzothiazole. The product was removed by filtration, washed with water and ethanol and air dried. The tan solid (90 g., 74%) was recrystallized from dimethylformamide/water to provide an analytical sample which melted at 205°–207°.

Anal. Calcd. for $C_8H_4ClN_3S_2$: C, 39.75; H, 1.67; N, 17.37.

Found: C, 39.63; H, 1.97; N, 17.13.

A mixture of the above compound (36.5 g., 0.15 mole) in dimethylformamide (500 ml.) was treated with phenyl isocyanate (18.0 g., 0.15 mole) and was heated on a steam bath with stirring for 5 hours. The mixture was poured into ice water (3 liters) and the precipitated yellow solid was removed by filtration and air dried to give 43 g. (79%) of product.

Several recrystallizations from dimethylformamide-methanol provided an analytical sample which melted at 330° with prior softening.

Anal. Calcd. for $C_{15}H_9ClN_4OS_2$: C, 49.93; H, 251; N, 12.63.

Found: C, 49.60; H, 2.51; N, 15.75.

EXAMPLE III

6-Chloro-2-[3-(p-nitrophenyl)ureido]-4-thiocyanatobenzothiazole

A mixture of 2-amino-6-chloro-4-thiocyanatobenzothiazole (36.5 g., 0.15 mole) and p-chlorophenyl isocyanate (23 g., 0.15 mole) in dimethylformamide (500 ml.) was heated on a steam bath with stirring for 5 hours. The mixture was diluted with water to give a yellow solid (40 g., 67%).

Recrystallization several times from nitromethane/dimethylformamide provided an analytical sample which decomposed above 240°.

Anal. Calcd. for $C_{15}H_8Cl_2N_4OS_2$: C, 45.57; H, 2.04; N, 14.18.

Found: C, 45.25; H, 2.07; N, 14.41.

EXAMPLE IV

2-[3-(p-Bromophenyl)ureido]-4-methoxy-6-thiocyanatobenzothiazole

To a stirred mixture of 2-amino-4-methoxy-6-thiocyanatobenzothiazole (48 g., 0.2 mole) in 320 ml. of dimethylformamide was added all at once p-bromophenylisocyanate (40 g., 0.2 mole). After addition was complete the stirred solution was heated on a steam bath for 5 hours. The solution was treated with water to the cloud point, chilled and then was filtered to give after air drying (77 g., 88.5%) of yellow solid.

An analytical sample was prepared by one recrystallization from methanol/dimethylformamide m.p. 245°–247° C.

Anal. Calcd. for $C_{16}H_{11}BrN_4O_2S_2$: C, 44.14; H, 2.55; N, 12.87.

Found: C, 43.86; H, 2.58; N, 12.85.

EXAMPLE V

2-[3-(p-Bromophenyl)ureido]-6-(n-butyl)-4-thiocyanatobenzothiazole

A solution of NaSCN (81 g, 1.0 mole) in methanol (300 ml) was chilled to −7° in an ice-salt bath. The stirred solution was treated dropwise with bromine (90 g, 0.57 mole) in NaBr saturated methanol (150 ml). After all the bromine had been added, p-butylaniline (30 g, 0.2 mole) was poured into the reaction mixture. The mixture was stirred for 4.5 hours, then filtered and poured into 400 ml of water. After neutralization with $NH_4OH$, the 2-amino-6-(n-butyl)-4-thiocyanatobenzothiazole was removed by filtration and recrystallized from methanol to give cream colored needles (37 g, 71%) which milted at 167°–169°.

Anal. Calcd. for $C_{12}H_{13}N_3S_2$: C, 54.72; H, 4.97; N, 15.96.

Found: C, 54.43; H, 4.97; N, 15.89.

To a stirred mixture of the above compound (53 g, 0.2 mole) in 320 ml. of dimethylformamide was added all at once p-bromophenyl isocyanate (40 g, 0.2 mole). After addition was complete, the stirred solution was heated on a steam bath for 4 hours. The solution was then reacted with water to the cloud point, and filtered to give after air drying (92 g, 99.3%).

An analytical sample was prepared by two recrystallizations from methanol/dimethylformamide, two recrystallizations from acetic acid, and one washing in hot nitromethane. The white solid melted at 260° C.

Anal. Calcd. for $C_{19}H_{17}BrN_4OS_2$: C, 49,48; H, 3.71; N, 12.14.

Found: C, 49.17; H, 3.77; N, 11.91.

EXAMPLE VI 6,7-Dichloro-2-[3-(p-chlorophenyl)ureido]-4-thiocyanatobenzothiazole p-Chlorophenyl isocyanate (15.3 g., 0.10 mole) was added in portions to a solution of 27.6 g. (0.10 mole) of 2-amino-6,7-dichloro-4-thiocyanatobenzothiazole in 300 ml. of dimethylformamide. The solution was heated at 120° with stirring for 5 hours and then cooled at 0° overnight. The solid was collected by filtration to give 22 g. (51%) of product. Recrystallization from ethanol gave an analytical sample, m.p. 238°–239°.

Anal. Calcd. for $C_{15}H_7Cl_3N_4OS_2$: C, 41.92; H, 1.64; N, 13.04.

Found: C, 41.70; H, 1.66; N, 12.96.

EXAMPLE VII

2-[3-(p-Bromophenyl)ureido]-6,7-dichloro-4-thiocyanatobenzothiazole p-Bromophenyl isocyanate (20 g., 0.10 mole) was added in portions to a solution of 27.6 g. (0.10 mole) of 2-amino-6,7-dichloro-4-thiocyanatobenzothiazole in 300 ml. of dimethylformamide. The solution was heated at 100° with stirring for 4½ hours and cooled at 0° overnight. The solid was collected by filtration. The filtrate was poured into ice water and the solid was collected by filtration. The combined solids were recrystallized from a methanol-dimethylformamide-water mixture to give 22 g. (50%) of product. Recrystallization from ethanol gave an analytical sample, m.p. 243°–245°.

Anal. Calcd. for $C_{15}H_7BrCl_2N_4OS_2$: C, 37.99; H, 1.49; N, 11.82.

Found: C, 37.69; H, 1.45; N, 11.77.

EXAMPLE VIII 6,7-Dichloro-2-[3-(3,4-dichlorophenyl)ureido]-4-thiocyanatobenzothiazole 3,4-Dichlorophenyl isocyanate (18.8 g., 0.10 mole) was added in portions to a solution of 27.6 g. (0.10 mole) of 2-amino-6,7-dichloro-4-thiocyanatobenzothiazole in 200 ml. of dimethylformamide. The solution was heated at 110° for 5 hours with stirring and cooled at 0° overnight. The solid was collected by filtration to give 28 g. (60%) of product. Two recrystallizations from ethanol gave 13 g. (28%) of analytical material, m.p. 313°–320° (dec.).

Anal. Calcd. for $C_{15}H_6Cl_4N_4OS_2$: C, 38.81; H, 1.30; N, 12.07.

Found: C, 38.66; H, 1.35; N, 12.13.

EXAMPLE IX 6,7-Dichloro-2-[3-(p-fluorophenyl)ureido]-4-thiocyanatobenzothiazole p-Fluorophenyl isocyanate (13.7 g., 0.10 mole) was added dropwise to a solution of 27.6 g. (0.10 mole) of 2-amino-6,7-dichloro-4-thiocyanatobenzothiazole in 200 ml. of dimethylformamide. The solution was heated at 120° for 5 hours with stirring and was cooled at 0° overnight. The solid was collected by filtration to give 26 g. (63%) of product. Two recrystallizations from nitromethane gave an analytical sample, m.p. 308°–310° (dec.).

Anal. Calcd. for $C_{15}H_7Cl_2FN_4OS_2$: C, 43.59; H, 1.70; N, 13.56.

Found: C, 43.23, H, 1.77; N, 13.55

What is claimed is:

1. A compound of the formula:

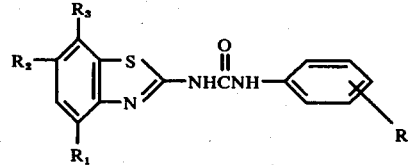

wherein R is hydrogen, 4-bromo, 4-chloro, 4-flouro, 3,4-dichloro, or 4-nitro; $R_1$ is methoxy or thiocyanato; $R_2$ is n-butyl, chloro, methyl, or thiocyanato; $R_3$ is hydrogen or chloro and at least one of $R_1$ and $R_2$ is thiocyanato.

2. The compound 6-methyl-2-[3-(p-nitrophenyl)ureido]-4-thiocyanatobenzothiazole.

3. The compound 6-chloro-2-(3-phenylureido)-4-thiocyanatobenzothiazole.

4. The compound 6-chloro-2-[3-(p-chlorophenyl)ureido]-4-thiocyanatobenzothiazole.

5. The compound 2-[3-(p-bromophenyl)ureido]-4-methoxy-6-thiocyanatobenzothiazole.

6. The compound 2-[3-(p-bromophenyl)ureido]-6-(n-butyl)-4-thiocyanatobenzothiazole.

7. The compound 6,7-dichloro-2-[3-(p-chlorophenyl)ureido]-4-thiocyanatobenzothiazole.

8. The compound 2-[3-(p-bromophenyl)ureido]-6,7-dichloro-4-thiocyanatobenzothiazole.

9. The compound 6,7-dichloro-2-[3-(3,4-dichlorophenyl)ureido]-4-thiocyanatobenzothiazole.

10. The compound 6,7-dichloro-2-[3-(p-fluorophenyl)ureido]-4-thiocyanatobenzothiazole.

* * * * *